United States Patent
Tran et al.

(10) Patent No.: US 11,071,710 B2
(45) Date of Patent: Jul. 27, 2021

(54) LICORICE EXTRACT SYNERGY WITH MENTHOL FOR BREATH FRESHENING IN A CONFECTIONARY PRODUCT

(71) Applicant: WM. WRIGLEY JR. COMPANY, Chicago, IL (US)

(72) Inventors: Lisa Tran, Chicago, IL (US); Lilian Ramirez, Chicago, IL (US); Barbara Stawski, Lake Villa, IL (US); Minmin Tian, Naperville, IL (US)

(73) Assignee: WM. WRIGLEY JR. COMPANY, Chicago, IL (US)

( * ) Notice: Subject to any disclaimer, the term of this patent is extended or adjusted under 35 U.S.C. 154(b) by 0 days.

(21) Appl. No.: 16/603,442

(22) PCT Filed: Apr. 16, 2018

(86) PCT No.: PCT/US2018/027713
§ 371 (c)(1),
(2) Date: Oct. 7, 2019

(87) PCT Pub. No.: WO2018/194948
PCT Pub. Date: Oct. 25, 2018

(65) Prior Publication Data
US 2020/0306173 A1    Oct. 1, 2020

Related U.S. Application Data (60) Provisional application No. 62/487,144, filed on Apr. 19, 2017.

(51) Int. Cl.
| | |
|---|---|
| *A61K 36/484* | (2006.01) |
| *A61K 8/9789* | (2017.01) |
| *A23G 3/48* | (2006.01) |
| *A61K 8/34* | (2006.01) |
| *A61Q 11/00* | (2006.01) |

(52) U.S. Cl.
CPC .............. *A61K 8/9789* (2017.08); *A23G 3/48* (2013.01); *A61K 8/34* (2013.01); *A61Q 11/00* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 1,484,415 A | 2/1924 | Shepherd | |
| 5,900,251 A | 5/1999 | Raissen | |
| 7,214,396 B2 * | 5/2007 | Rivier | A23G 4/06 426/72 |
| 2004/0247669 A1 * | 12/2004 | Gin | A23G 3/368 424/468 |
| 2014/0227388 A1 * | 8/2014 | Nissen | A24B 15/18 426/5 |

FOREIGN PATENT DOCUMENTS

| | | | |
|---|---|---|---|
| CN | 104666428 | * | 6/2015 |
| DE | 2606533 A1 | | 8/1976 |
| EP | 2520278 A1 | | 11/2012 |
| GB | 2068730 A | | 8/1981 |
| IN | 2000 MU00015 | * | 8/2006 |
| WO | 9205766 A1 | | 4/1992 |
| WO | WO 92/05766 | * | 4/1992 |
| WO | 2016044470 A1 | | 3/2016 |

OTHER PUBLICATIONS

Mintel, 2 in 1 Oral Care Foam XP-002784136, Jan. 31, 2011, pp. 1-4, Database GNPD.
Mintel, Breath Freshening Sweets XP-002784135, Feb. 28, 2006, p. 1-2, Database GNPD.

* cited by examiner

*Primary Examiner* — Ralph J Gitomer (57) ABSTRACT

Breath freshening formulations comprising licorice extract and menthol are provided. The breath freshening formulations can provide breath freshening in a confectionary product, through the synergy between licorice extract and menthol. Methods of reducing sulfurous compounds over time via a chewy confectionary product are also provided.

9 Claims, 4 Drawing Sheets

LICORICE EXTRACT SYNERGY WITH MENTHOL FOR BREATH FRESHENING IN A CONFECTIONARY PRODUCT

CROSS REFERENCE TO RELATED APPLICATIONS

This application is a U.S. National Stage Application under 35 U.S.C. 371 of International Patent Application No. PCT/US2018/027713, filed on Apr. 16, 2018, which claims priority to U.S. Provisional Application No. 62/487,144, filed Apr. 19, 2017, the contents of each of which are incorporated by reference herein in their entirety.

FIELD

The presently disclosed subject matter relates to breath freshening formulations, particularly for use in confectionary products. Specifically, the present disclosure is directed to breath freshening compositions and methods of reducing sulfurous compounds that include synergy of licorice extract and menthol in a confectionary product.

BACKGROUND

The presence of microbes in the oral cavity can cause malodor or bad breath. For example, oral bacteria can excrete waste products with malodorous compounds including hydrogen sulfide, methyl mercaptan, and dimethyl sulfide. Such volatile sulfurous compounds (VSCs) are responsible for causing bad breath in the oral cavity.

As such, it is desirable to provide consumer products that can reduce malodors and freshen breath. Breath freshening is a desired consumer sensory attribute for numerous consumer products, both edible compositions and other oral products. To date, many efforts have been directed at masking the effect of VSCs using a scented or cooling product. For example, licorice extra has been used to freshen breath. Similarly, menthol has also been used to impart breath freshening and cooling effects. However, it is more desirable to reduce the presence or production of VSCs in order to counteract the effects of oral bacteria.

Thus, there remains a need in the art for a breath freshening formulation that significantly reduces the production of VSCs. The presently disclosed subject matter addresses these and other needs as discussed in detail below.

SUMMARY OF THE INVENTION

The presently disclosed subject matter provides breath freshening compositions comprising licorice extract and menthol. It was surprisingly found that compositions having these components exhibited a synergistic effect and were able to reduce the production of volatile sulfurous compounds (VSCs) in an oral cavity.

In certain aspects, the present disclosure provides breath freshening compositions comprising licorice extract and menthol. For example, and not as a limitation, the licorice extract can be present in an amount of from about 0.5 wt-% to about 20 wt-%, preferably in an amount of about 10 wt-%. The menthol can be present in an amount of about 0.05 wt-%. In particular embodiments, the breath freshening composition can comprise about 10 wt-% licorice extract and about 0.05 wt-% menthol.

In certain embodiments, the menthol can be (−)-Menthol. For example and not limitation, the (−)-Menthol can be derived from a plant of the genus *Mentha*. Alternatively or additionally, the licorice can be derived from *Glycyrrhiza glabra*.

The present disclosure further provides consumer products comprising such breath freshening compositions. For example, the consumer product can be selected from the group consisting of a food product, a confectionary product, and an oral product. In certain embodiments, the confectionary product is a chewy candy.

As embodied herein, the breath freshening composition is present in a consumer product in an effective amount to reduce the production of a sulfurous compound in an oral cavity. For example, the sulfurous compound can be a VSC such as hydrogen sulfide ($H_2S$).

Methods of reducing the production of hydrogen sulfide in an oral cavity are also provided. Such methods include introducing to the oral cavity a consumer product comprising a breath freshening composition comprising licorice extract and menthol. In certain embodiments, the breath freshening composition can include about 10 wt-% licorice extract and about 0.05 wt-% menthol. The consumer product can be selected from the group consisting of a food product, a confectionary product, and an oral product. In certain embodiments, the confectionary product can be a chewy candy.

The foregoing has outlined broadly the features and technical advantages of the present application in order that the detailed description that follows can be better understood.

Additional features and advantages of the application will be described hereinafter which form the subject of the claims of the application. It should be appreciated by those skilled in the art that the conception and specific embodiment disclosed can be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIG. 1 shows the $H_2S$ produced after mixing with licorice extract powder alone, menthol alone, and a combination of licorice extract powder and menthol combined.

DETAILED DESCRIPTION

As noted above, there remains a need in the art for breath freshening compositions that reduce the production of volatile sulfurous compounds (VSCs) that cause bad breath in the oral cavity. The presently disclosed subject matter addresses this need through a breath freshening combination of licorice extract and menthol that has a unique synergy to decrease VSC production as compared to either component alone.

1. Definitions

The terms used in this specification generally have their ordinary meanings in the art, within the context of this disclosed subject matter and in the specific context where each term is used. Certain terms are discussed below, or elsewhere in the specification, to provide additional guidance to the practitioner in describing the compositions and methods of the disclosed subject matter and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value.

Unless otherwise specified, all percentages used herein are weight percents.

As used herein, "admixing" refers to the process where the breath freshening formulation is mixed with or added to the completed product, or mixed with some or all of the components of the product during product formation, or some combination of these steps. When used in the context of admixing, the term "product" refers to the product or any of its components. This admixing step can include a process selected from the step of adding the breath freshening formulation to the product, suspending the breath freshening formulation in the product, encapsulating the product with the breath freshening formulation, mixing the breath freshening formulation with the product, and any combination thereof. The breath freshening formulation can be a liquid, dry powder, spray, paste, suspension, and any combination thereof.

As used herein, "food product" or "food product composition" includes ingestible products including but not limited to human foods, animal or pet foods, pharmaceutical products, and consumer products.

As used herein, the term "confectionary product" refers to a sweet or dessert edible composition. Confectionary products can include, but are not limited to, cakes, cookies, pies, candies (hard and soft), compressed mints, chewing gums, gelatins, ice creams, sorbets, jams, jellies, chocolates, fudge, fondant, liquorice, taffy, and combinations thereof.

As used herein, the term "chewing gum" or "gum" refers to a flavored substance intended for chewing. The term as used herein also includes bubble gum and confectionary products containing chewing gum. In certain embodiments, chewing gum forms include, but are not limited to, tablets, sticks, solid balls, hollow balls, cut and wrap, and pellets or pillows. As used herein, chewing gum contains a water insoluble gum base portion and a water soluble bulk portion.

As used herein, the term "compressed mint" refers to a hard confectionary product that requires sufficient strength to bite and/or shatter and primarily dissolves in the mouth by sucking.

As used herein, the term "lozenge" refers to a flavored tablet intended to be dissolved slowly in the mouth, and can soothe or provide temporary relief and lubrication to the throat.

As used herein, "flavor" shall include aroma, odor and/or taste. The presently disclosed breath freshening compositions can be used to impart flavor to a food product and can be in a variety of forms including but not limited to a liquid, dry powder, spray, paste, suspension, other solid form, and any combination thereof. The flavor can be a natural composition, an artificial composition or any combination thereof.

As used herein, the term "breath freshening agent" means compounds or compositions that counteract malodor. Breath freshening agents include, but are not limited to, salts of zinc, salts of copper, polyphenols, mushroom extracts, and mixtures thereof.

As used herein, "licorice extract" refers to a composition comprising one or more chemical compounds extracted from the licorice plant *Glycyrrhiza* spp. In certain embodiments, the licorice extract is an extract produced as described herein. In certain embodiments the extract comprises a glycyrrhizol and/or glycyrrhizin.

As used herein, the terms "synergistic effect," "synergistic interaction," or "synergistic enhancement" refers to the surprising and unexpected effect when two chemical compounds taken together is greater than the sum of each chemical compound's separate effect at the same amount and/or level.

2. Licorice Extract

Licorice comes from the genus *Glycyrrhiza*, which consists of about 30 species (Nomura et al. (2002) Pure Appl. Chem. 74: 1199-1206), some of which have been used by humans (Wang and Nixon (2001) Nutr. Cancer, 39: 1-11). Licorice is the name typically applied to the roots and stolons of *Glycyrrhiza* species. *Glycyrrhiza uralensis* is one of the most frequently used traditional medicines in mainland China and in some other countries as well.

Generally, extraction of the licorice roots is made with hot water and steam. To reduce the water content, licorice juice is evaporated, concentrated, and subsequently cooked under continuous stirring. Licorice extract can be further processed by pulverizing in a spray tower. Extracts can be in the form of a liquid, semiliquid or syrup, or a solid, such as a dry powder. Alternatively, licorice extract can be re-heated and cast into licorice blocks.

Certain licorice extracts have been used to treat various diseases. Many interesting chemical molecules have been identified from the herb that are associated with various therapeutic effects. One main active component in licorice roots, glycyrrhizin, is a sweet glycoside. Glycyrrhizin has antimicrobial effects that can inhibit formation of dental caries by inhibiting bacterial adherence. Also, licorice extract can kill other pathogenic bacteria. For example, the extract has activity against the bacteria involved in both periodontitis and halitosis, and is useful in treating/mitigating these conditions. As a dry powder with consistent antimicrobial activity, licorice extract can be used for many applications, such as, but not limited to, expanded dental applications, e.g., tea, toothpick coatings, dental floss coatings, toothpaste, gel, mouthwash, varnish, and even professional dental products.

Of note in the presently disclosed subject matter, licorice extract in combination with menthol has been found to decrease production of VSCs that are responsible for causing bad breath in the oral cavity. In particular, embodiments of the present disclosure use licorice powder extracted from *Glycyrrhiza glabra*. Non-limiting examples include licorice extract or licorice extract powder with the following properties in Table 1.

TABLE 1

| Measurement | Level |
| --- | --- |
| Glycyrrhicinic Acid (HPLC method) | >5.5% |
| Cane Sugar | 10% |
| Moisture | 6.50% |
| Insolubles (Hot Water) | 5% |
| Ash Content | 14% |
| pH | 4.5-6.0% |

In various embodiments, carrier agents can provide retention and sustained release of the licorice extract for reducing sulfurous compound production. In certain embodiments, the licorice extract and the carrier agent are in the form of an admixture.

In certain embodiments, the licorice extract described herein is incorporated into a breath freshening formulation. Such formulations can be used in consumer oral products such as, but not limited to, compressed mints, chewing gum, chewy candy, lozenges, toothpaste, mouthwash, tooth whitening strips or solutions, dental floss, toothpicks, toothbrush bristles, oral sprays, and the like. The formulation of such oral products is known to those of skill in the art, and the licorice extract of the present disclosure is added in synergistic combination with menthol.

3. Menthol

In certain non-limiting embodiments, the breath freshening formulation comprises menthol. For example, the menthol can be a compound having the following structure:

1-Methanol; MW = 156

The menthol of the presently disclosed subject matter can be a pure stereoisomer (e.g., (−)-Menthol) or a combination of more than one stereoisomers. For example, and not limitation, the stereoisomers can include one or more of (−)-Menthol, (+)-Menthol, (+)-Isomenthol, (+)-Neomenthol, (+)-Neoisomenthol, (−)-Isomenthol, (−)-Neomenthol, and (−)-Neoisomenthol.

As embodied herein the menthol can be derived from synthetic or natural sources. For example, the menthol can be chemically synthesized or derived from biosynthesis. Alternatively or additionally, the menthol can be extracted from a natural source. For the purpose of example, natural sources of menthol include, but are not limited to, plants in the family Lamiaceae. For example, in certain embodiments, the menthol can be derived from a plant in the *Mentha* genus, such as peppermint, spearmint, ginger mint, pineapple mint, woolly mint, pennyroyal, catmint, lavender mint, grapefruit mint, licorice mint, basil mint, watermint, and calamint. In particular embodiments, the menthol is derived from a peppermint plant.

4. Breath Freshening Formulations

While licorice extract individually reduces oral bacteria that produces sulfur compounds causing bad breath, the present disclosure has found that in combinations with menthol, a synergistic effect is produced. This synergistic effect reduces the production of sulfurous compounds significantly, and more than the expected net cumulative effect of licorice extract or menthol individually. In certain embodiments, methods of reducing the incidence, duration, or severity of sulfurous compound production are provided. The methods can include incorporating licorice extract synergistically with menthol in a breath freshening formulation.

The breath freshening formulations of the present disclosure can include particular amounts of licorice extract and menthol. In particular embodiments, the licorice extract is licorice extract powder. For example, the licorice extract can be present in the breath freshening formulation in an amount of from about 0.5 wt-% to about 20 wt-%, or from about 3 wt-% to about 10 wt-%, or from about 4 wt-% to about 10 wt-%, or from about 5 wt-% to about 10 wt-%, or from about 6 wt-% to about 10 wt-%, or from about 7 wt-% to about 10 wt-%, or from about 8 wt-% to about 10 wt-%. In particular embodiments, the licorice extract is present in an amount of about 10 wt-%.

The breath formulation can further include menthol. For example, the menthol can be present in the breath freshening formulation in an amount of from about 0.01 wt-% to about 0.1 wt-%, for example, about 0.05 wt-%.

Additionally or alternatively, the licorice extract and menthol can be present in a particular ratio. For example and not limitation, the ratio of licorice extract to menthol in the breath freshening formulation can be no more than about 5:1, no more than about 10:1, or no more than about 20:1.

As embodied herein, the breath freshening formulation can further include additional compounds. For example, in certain non-limiting embodiments, additional compounds include, but are not limited to, other chemicals, such as flavoring agents, that add additional flavor characteristics. Flavoring agent can be used in liquid or solid form. Flavoring agents can include artificial or natural flavors known in the art, for example, synthetic flavor oils; natural flavoring aromatics and/or oils; oleoresins; extracts derived from plants, leaves, flowers, fruits, fruit flavors, and the like; or a combination thereof. Non-limiting representative flavors include oils such as cinnamon oil, clove oil, bay oil, anise oil, *eucalyptus* oil, thyme oil, cedar leaf oil, oil of nutmeg, allspice, oil of sage, mace, oil of bitter almonds, *cassia* oil, and citrus oils including lemon, orange, lime, grapefruit, vanilla, fruit essences, including apple, pear, peach, grape, strawberry, raspberry, blackberry, cherry, plum, pineapple, apricot, banana, melon, tropical fruit, mango, mangosteen, pomegranate, *papaya*, honey lemon, and the like or a combination thereof. Artificial flavor components are also contemplated by the present disclosure. Those of ordinary skill in the art will recognize that natural and artificial flavors can be combined in any sensorially acceptable blend. All such flavors and blends are contemplated by the presently disclosed subject matter.

As embodied herein, the presently disclosed breath freshening formulations can reduce the production of volatile sulfurous compounds (VSCs) in an oral cavity. Such VSCs include, but are not limited to, hydrogen sulfide ($H_2S$). For example, $H_2S$ production can be reduced in the presence of the disclosed breath freshening compositions as compared to $H_2S$ production in the absence of the disclosed breath freshening compositions. Thus, the presently disclosed breath freshening formulations can reduce the source of a malodor in an oral cavity in addition to masking the effects of such malodors.

The breath freshening formulations of the presently disclosed subject matter can be used in various consumer products, including food products, confectionary products, oral products, dentifrice, toothpaste, mouthwash, mouth spray, tobacco, and pharmaceuticals. The breath freshening formulations can impart breath freshening or cooling effects to the consumer product. In certain embodiments of the present application, the breath freshening formulation is added to the consumer product in an amount effective to provide the desired flavor and/or effects. The presently disclosed subject matter can be incorporated into oral products using conventional procedures and equipment and suitable additional components known in the art.

In certain embodiments, breath freshening formulations of the presently disclosed subject matter can be incorporated into oral products including, but are not limited to dentifrice, toothpaste, mouthwash, mouth spray, tobacco, and pharmaceuticals.

5. Chewy Candies and Confections

The breath freshening formulations of the presently disclosed subject matter can be incorporated into confectionary products including, but not limited to, cakes, cookies, pies, candies (hard and soft), compressed mints, chewing gums, gelatins, ice creams, sorbets, jams, jellies, chocolates, fudge, fondant, liquorice, taffy, and combinations thereof.

In particular, chewy candies are opaque and generally firm, having an elastic texture that appeals to consumers. As a chewy confection is chewed, it does not break apart, but dissolves slowly in the mouth. These smaller confection pieces deliver flavor and sweetness as they dissolve into a pliable chewy substance in the mouth.

Chewy confection is a food product that is formed by (a) mixing a sweetener solution (generally sugar and corn syrup), (b) creating a hydrated suspension containing water and a gelling agent, (c) combining the sweetener solution and gelling agent, and (d) then adding a fat mixture after whipping the sweetener mixture and gelling agent together, and aerating the formed product by forming the mass into a finished piece.

Chewy confectionary products are typically made with a sweetener bulking agent and a texturizing agent. Commonly used sweeteners are sucrose and glucose syrup or corn syrup. A fat is also commonly added to such chewy confectionary products to achieve desired chew characteristics. Chewy confectionaries have a cohesive nature under normal room conditions. A chewy confectionary product can further include water, foaming agents, humectants, artificial and natural sweeteners, emulsifiers, flavor enhancers, acids, artificial and natural flavorings, colorings, fruit juices, vegetable juices, proteins, and other additives typically used in the production of chewy confectionary products as desired. Often, chewy confectionary products are referred to as chewy candy, toffee, gummies, or taffy.

A variety of sweetener bulking agents can also be used besides sucrose. Other sugars that can be used are dextrose; maltose; lactose; galactose; tagatose; various types of glucose syrups such as corn and rice; and high fructose. For a low calorie product, alditols or polyols can be used such as sorbitol, mannitol, maltitol, isomalt, erythritol, and various types of hydrogenated starch hydrolyzates (HSH). The sweetener can be added to the chewy confectionary product in the amount of about 10 wt-% to about 99 wt-% of the chewy confectionary product. Fats can be added to the chewy confectionary product in the amount of about 0.5 wt-% to about 25 wt-% by weight of the chewy confectionary product.

Chewy confections typically contain gelatin, egg white (albumin), starch, or combinations thereof as the texturizing agent so that they have the chewy texture that is desirable for the products. Gelatin is the most popular of the texturizing agents as it gives the chewy confectionary products a long lasting cohesive chew. Food grade gelatin is obtained from bovine or porcine raw materials, and is thus undesirable to a number of consumer groups who observe certain dietary restrictions. Additionally, since gelatin is a protein, it is highly sensitive to temperature and/or acid, which can cause it to degrade and foul.

Egg white, also known as albumin, is also traditionally used as a texturizing agent. However, similar to gelatin, albumin is also an animal product, and is thus undesirable to a number of consumer groups who observe certain dietary restrictions. Because egg white is also a protein, there are also processing limitations similar to those associated with gelatin when using egg white as the texturizing agent.

Starches are also traditionally used as texturizing agents; however, they typically have a low gelling tendency and are not as useful alone in creating the ideal chewy texture in a chewy confectionary product. Starches will most often be used in conjunction with gelatin to achieve the desired chewy texture and consistency for a chewy confectionary product.

Typically when gelatin is used as the texturizing agent, water, glucose syrup, and sucrose are first cooked together and then combined with a hydrated gelatin to achieve a mixture containing the desired moisture target of the final chewy confectionary product. When using gelatin, there are temperature and time limitations with regards to exposure to high heat. Gelatin must be added at either a low heat or added quickly at high heat (i.e., the gelatin is not exposed to the high heat for a long period of time) so as to not degrade or foul the gelatin. Starch and other previously mentioned commonly used ingredients in chewy confectionary products can further be added to the mixture to achieve the desired texture, color, and taste. Then the mixture is poured into molds to form while cooling.

Typically when egg white is used as the texturizing agent a fresh, pasteurized or rehydrated egg white is beaten into a foam with or without other ingredients. The foam is then set by cooking or by combining it with a hot carbohydrate syrup. Other commonly used chewy confectionary product ingredients can then be further added to the mixture.

Typically when starch is used as the texturizing agent, water, glucose syrup, and the starch are pre-mixed and heated to a desired temperature and then cooked at that temperature until the starch has gelatinized, forming a starch gel. Both modified and unmodified starches can act as gelling agents in confectionary applications. Starch is basically long polymers of glucose units (also known as dextrose) that are arranged into discrete, highly organized, semi-crystalline aggregates called "starch granules." These starch polymers within the "granule" are either straight-chain/linear (amylose) or highly branched (amylopectin). Starches vary by source in their amylopectin-to-amylose ratios.

When a starch is gelatinized, the crystalline structure of the granules is lost. The granules begin to swell, take up water, and/or increase in size, increasing the viscosity of the aqueous system. The starch granules fully cook out in the candy-making process, to the point where the granules lose integrity, fragment, and/or rupture. As this cooked starch cools, the solubilized straight-chain amylose polymers realign tightly to form a gel.

When the starch has gelatinized, the confectionary product is cooled and transferred to a mixer where the remaining ingredients are added (gelatin, fat, emulsifiers, acid, flavors, etc.), and mixed until the desired density or texture is reached. The texture of the candy can be altered by whipping air into it rather than pulling it if a lighter texture is desired. A foaming agent can also be used to add texture to a traditional chewy confectionary product. The chewy confectionary product is then rolled and cut into the desired shapes and sizes. The cut candy can then be packaged into appropriate packaging for distribution.

As mentioned, besides being used as the sole gelling agent in traditional chewy confectionary products, some starches can also be used to partially replace and/or complement gelatin in gummy-type candies where a softer, less chewy and/or less elastic texture is desired or to as texturizing agent.

Starch can also be used to replace or complement more expensive and/or harder-to-source ingredients such as gelatin or gum Arabic. Starch can help to modify the chew characteristics of the candy (i.e., increasing the structure and/or body, softness, chewiness, and elasticity of the candy while reducing "toothstick"). Starch has also been found to help inhibit sugar recrystallization and reduce cold flow in traditional chewy confectionary products.

Cold flow is a common problem with traditional chewy confectionary products. "Cold flow" is defined as the distortion, deformation, or dimensional change which takes place in a material under ambient conditions and pressures with an inability to return to its original dimensions. When products cold flow, the shape of the product deforms causing inconsistent and distorted looking products which may not be very desirable to consumers. Often, cold flow becomes a problem during storage. Stickiness can also be a big problem for traditional confectionary products, causing products to stick or clump together in its packaging.

Each traditional texturizing agent has its own advantages. The advantage of using gelatin as the texturizing agent in chewy confectionary products is that the gelatin gives the candy a distinctive chewy texture that ranges from soft to very firm, depending on the amount of gelatin used. Using egg white as the texturizing agent helps stabilize incorporated air, thus keeping air bubbles from collapsing; this gives the product a light and airy texture. One of the advantages of using starch as the texturizing agent in such products is that it allows one to control the viscosity of the substance during production, which helps with control of subsequent cold flow during storage.

A recent advance in chewy confections is the elimination of egg albumin. This is replaced by the use of gelatin, starches, or other carbohydrates. Some of these carbohydrates are natural gums such as gum Arabic, xanthan gum, locust bean gum, gellan gum carrageenan, pectins; and new carbohydrates like Nutriose, indigestible dextrin, inulin, fructooligosaccharides (FOS), and polydextrose.

As embodied herein, the breath freshening formulations are preferably incorporated in a chewy confectionary product. The compositions of the presently disclosed subject matter are used in a chewy confectionary product. Nonlimiting examples of chewy confections include jellies, gummies, caramels, nougats, and taffies. The confections include a variety of shapes, flavors, textures, and sizes. Nonlimiting examples of jelly candy products include jellybeans, gummy bears, and licorice sticks. Caramels are emulsions of fat droplets in a syrup made of sugars and hydrated milk proteins. Nougats are nongrained, firm, chewy confections having a light aerated texture. Taffies are also aerated, usually by a pulling machine, to produce a confection with a high degree of chewiness.

For the chewy candy composition to give a longer chewing experience, it should include a material that would create a candy product that is tough, elastic, chewy, and of reduced solubility in water. Such materials include pectin, gelatin, cellulose gum, colloid gum (such as xanthan, carrageenan, or locust bean), substituted or crosslinked starches and/or other such long chain materials.

Chewy confectionary products can also include thickeners. Thickeners include corn syrup, gelatin, pectin, and other common thickeners and are added in amounts that achieve the desired organoleptic effect.

In one embodiment of the present disclosure, the candy product is a chewy candy product. The chewy candy product can include sugar, corn syrup, fat and optionally, gelatin, which provide the desired chewy texture. Preferably, the chewy candy product comprises gelatins and fats in the necessary amounts to achieve the target texture of the candy product.

In another embodiment of the present disclosure, the candy product is a gummy candy product. The gummy candy product can include sugar, corn syrup, gelatin and optionally, pectin, which provide the desired gummy texture. In an alternate embodiment of the present disclosure, the candy product comprises a soft chewy or a soft gummy candy product. The soft chewy gummy candy product includes sugar, corn syrup, and pectin—with pectin to achieve the desired soft chewy gummy texture.

In yet another alternate embodiment, the candy product comprises a pressed chewy product. The pressed chewy candy product can include sugar, corn syrup, and fat—which provides the desired chewy texture.

5.1 Mints

The presently disclosed subject matter can be incorporated into mint confectionaries, and more particularly into compressed mint products using conventional tablet pressing procedures and equipment and suitable additional components known in the art.

Compressed mints of the presently disclosed subject matter can contain sugar or can be sugar-free. In addition to the disclosed cooling compositions, other suitable flavoring agents can be included as well as ingredients that give a tingling sensation. In the case of products with multiple layers, each layer can have different flavoring agents or levels. In one embodiment, the compressed mint can comprise a coating layer covering at least a portion of the product. In that case, the coating layer can contain flavoring agents, or not.

The compressed mints can include one or more of the following: anti-microbial agents; physiological cooling agents; breath freshening agents; breath freshening and mouth odor masking flavors; dental active agents; and combinations thereof.

In certain embodiments, the compressed mint tablet further contains one or more additional compounds including but not limited to sorbitol (e.g., 90-99 wt-%), acesulfame K (e.g., 0.05-0.5 wt-%), sucralose (e.g., 0.05-0.5 wt-%), magnesium stearate (e.g., 0.5-2 wt-%), Neobee oil (e.g., 1-2 wt-%), peppermint oil (e.g., 0.5-2 wt-%), and combinations thereof.

5.2 Chewing Gum

The presently disclosed subject matter can also be incorporated into chewing gum. In certain embodiments, the chewing gum can be in the form of tablets, sticks, solid balls, hollow balls, cut and wrap, and pellets or pillows.

In certain embodiments, breath freshening compositions can be mixed and added to flavor, and then added to a gum mixture. In certain embodiments, breath freshening compositions can be added directly to the gum mixture. In other embodiments, breath freshening compositions can be encapsulated, or formulated in a coating layer to enhance release from the chewing gum.

A chewing gum center composition or other chewing gum compositions can contain a chewable gum base portion, which is essentially free of water and is water-insoluble, a water-soluble bulk portion, and flavors which can be water insoluble. The water-soluble portion can dissipate with a portion of the flavor over a period of time during chewing. The water-insoluble gum base portion is retained in the mouth throughout the chew.

In certain embodiments, the water-insoluble gum base can comprise elastomers, elastomer solvents, plasticizers, waxes, emulsifiers and/or inorganic fillers. Plastic polymers, such as polyvinyl acetate, which can behave as plasticizers, can also be included. In certain embodiments, plastic polymers can include but are not limited to, polyvinyl laureate, polyvinyl alcohol and polyvinyl pyrrolidone. Non-limiting examples of elastomers can include polyisobutylene, butyl rubber (isobutylene-isoprene copolymer), and styrene butadiene rubber, as well as natural latexes such as chicle. In certain embodiments, elastomer solvents can include resins such as terpene resins. In certain embodiments, the plasticizers are fats and oils, including but not limited to, tallow, hydrogenated and partially hydrogenated vegetable oils, and cocoa butter. In certain embodiments, the waxes include, but are not limited to, paraffin, microcrystalline and natural waxes such as beeswax and carnauba.

In certain embodiments, the chewing gum further contains one or more flavor components that are derived from artificial or natural sources or combinations thereof. In certain embodiments, the chewing gum can contain sugar, or can be sugar-free. In certain embodiments, the chewing gum can comprise high potency sweeteners including, but not limited to, synthetic substances, saccharin, thaumatin, alitame, saccharin salts, aspartame, sucralose, *stevia*, and acesulfame.

In certain embodiments, the chewing gum further contains one more coloring agents. In certain embodiments, the coloring agents can be food quality dyes.

In certain embodiments, suitable encapsulating materials can include, but are not limited to, water-soluble sugar or sugar alcohol such as sorbitol, isomalt, dextrose, erythritol, lactitol, maltitol, mannitol, xylitol, hydrogenated corn syrup and mixtures thereof. In certain embodiments, encapsulating materials can also include water soluble starch, modified starch, hydroxyl methyl cellulose, hydroxypropyl methylcellulose (HPMC), sodium alginate, alpha, beta and gamma cyclodextrin, polymers and combinations thereof. In certain embodiments, the coating compositions can be susceptible to water permeation to various degrees. In certain embodiments, the coating composition is a food grade material.

EXAMPLES

The presently disclosed subject matter will be better understood by reference to the following Examples, which are provided as exemplary of the disclosed subject matter, and not by way of limitation.

Example 1: Effect of Ingredients on Hydrogen Sulfide Production

This example evaluated the effect of breath freshening ingredients on hydrogen sulfide production by salivary bacteria.

Sample Preparation:
1. About 10-20 ml of saliva was obtained from human subjects and mixed together prior to use.
2. L-cysteine was dissolved in deionized (D.I.) water to produce 0.5% of cysteine solution.
3. About 2.5 ml of pooled saliva was mixed with 2.5 ml of cysteine solution in a 20 ml headspace vial.
4. The amount of hydrogen sulfide generated by salivary bacteria was analyzed by a gas chromatography (GC) equipped with a sulfur detector. Pooled saliva (50% dilution) and L-cysteine (0.25% in D.I water) were used as the negative controls.

Gas Chromatograph Analysis of Volatile Sulfur Compounds:
1. For evaluation of the headspace concentration of volatile sulfur compounds (VSCs), a gas chromatograph (GC) equipped with a sulfur chemiluminescence detector (SCD) was used.
2. Each run was completed within 10 minutes.
3. The level of $H_2S$ was analyzed by the GC-SCD by direct injection of 0.25 ml of headspace volume with an automated sampler.

Results:
Levels of $H_2S$ concentrations [μg/mL] were measured by gas chromatography-mass spectrometry (GC-MS). Licorice extract powder (*Glycyrrhiza glabra*) and menthol were each evaluated individually and then in combination. Saliva with cysteine served as a control reference. Licorice extract powder was sampled individually at 10 mg/ml and 20 mg/ml in a saliva-cysteine mixture. Menthol at 2 mg/ml was sampled individually. Three combinations of licorice and menthol were sampled, varying the amount of licorice extract.

Figure 1:
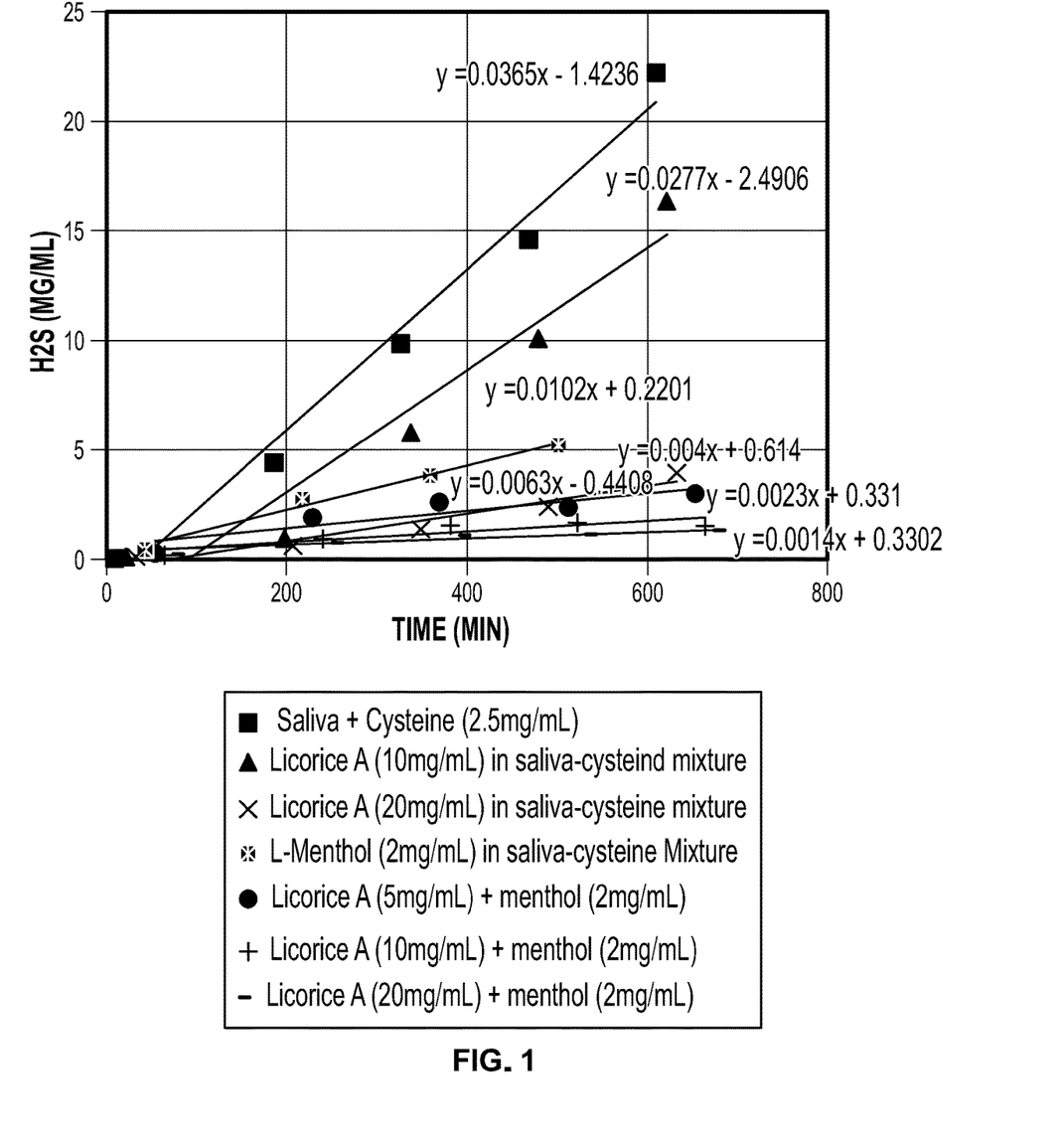
FIG. 1 compares the effect of ingredients and provides a graphical representation of the levels of hydrogen sulfide ($H_2S$) production [µg/ml] measured by gas chromatography-mass spectrometry (GC-MS) (y-axis) versus time after mixing (x-axis). In particular.

FIG. 1 shows that the synergistic combination of 20 mg/ml of licorice extract powder and 2 mg/ml of menthol in a 10:1 ratio showed decreased hydrogen sulfide ($H_2S$) production over time, compared to the ingredients individually. The results of this example show that a breath freshening composition comprising licorice extract powder and menthol in combination are suitable for oral or confectionary products to help reduce VSC production and bad breath over time.

Example 2: Ratio of Licorice Extract to Menthol on Hydrogen Sulfide Production This example compared various ratios of licorice extract powder to menthol on hydrogen sulfide production by measuring the peak gas chromatography area. Licorice A at 20 mg/ml and menthol at 4 mg/ml as individual ingredients were tested individually. 4 mg/ml of menthol, as compared to 2 mg/ml of menthol, showed a slight decrease of $H_2S$ production in later time points.

Figure 2:
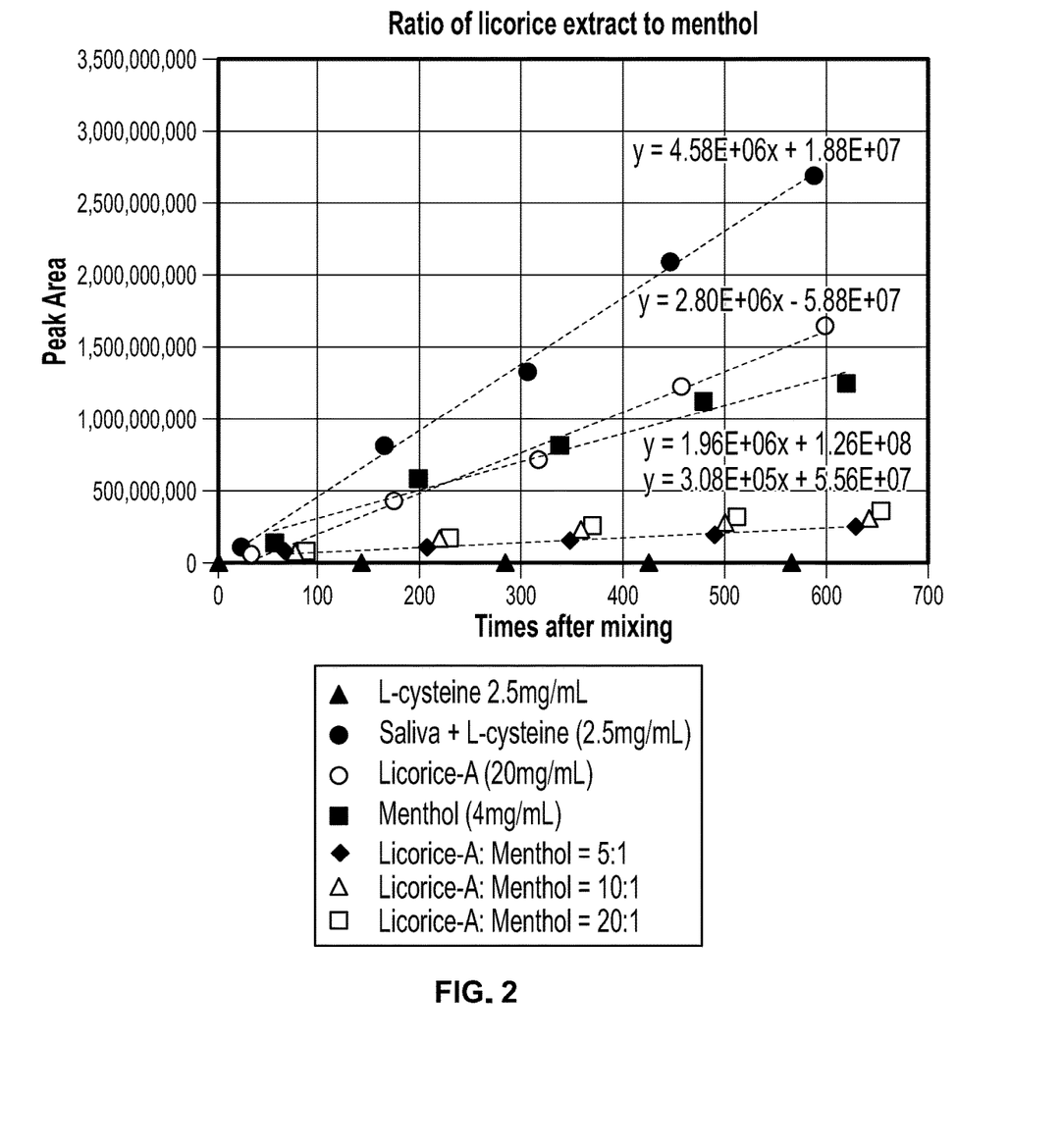
FIG. 2 provides a graphical representation of $H_2S$ production via GC-MS peak area (y-axis) versus time after mixing (x-axis) between different ratios of licorice extract powder to menthol, as compared to saliva, 1-cysteine, licorice extract powder alone, and menthol alone.

FIG. 2 shows that all tested ratios of licorice to menthol outperformed the single ingredients in terms of $H_2S$ production over time. The results of this example show that a breath freshening composition comprising licorice extract powder and menthol in combination, particularly at a ratio of 5:1, are suitable for chewy products and oral or confectionary products to help reduce VSC production and bad breath over time.

Example 3: Chewy Candy

Figure 3:
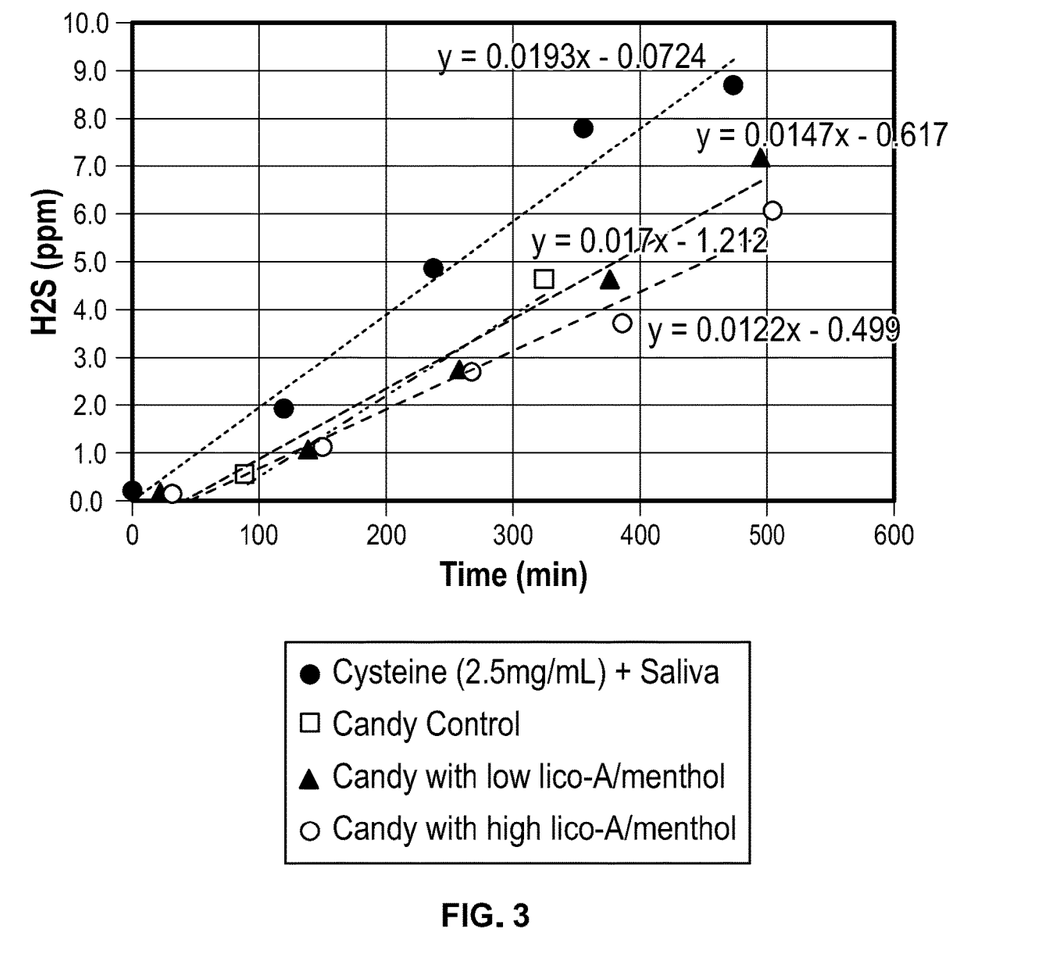
FIG. 3 provides a graphical representation of $H_2S$ produced (y-axis) over time (x-axis) in evaluating combinations of licorice extract powder and menthol in a sugar-free chewy candy matrix.

Licorice extract powder and menthol in combination was evaluated in a sugar-free chewy candy matrix. In FIG. 3, the licorice-menthol combination was evaluated at 2 wt-% of the formula and 10 wt-% of the formula. Both combinations were blended with menthol (0.05 wt-%). A licorice-menthol combination outperformed the control chewy candy formulation (formulated without menthol or licorice powder) in terms of decreased $H_2S$ production over time. This example shows that a breath freshening formulation of the present disclosure are suitable for use in a chewy candy product.

Example 4: Compressed Mint

Figure 4:
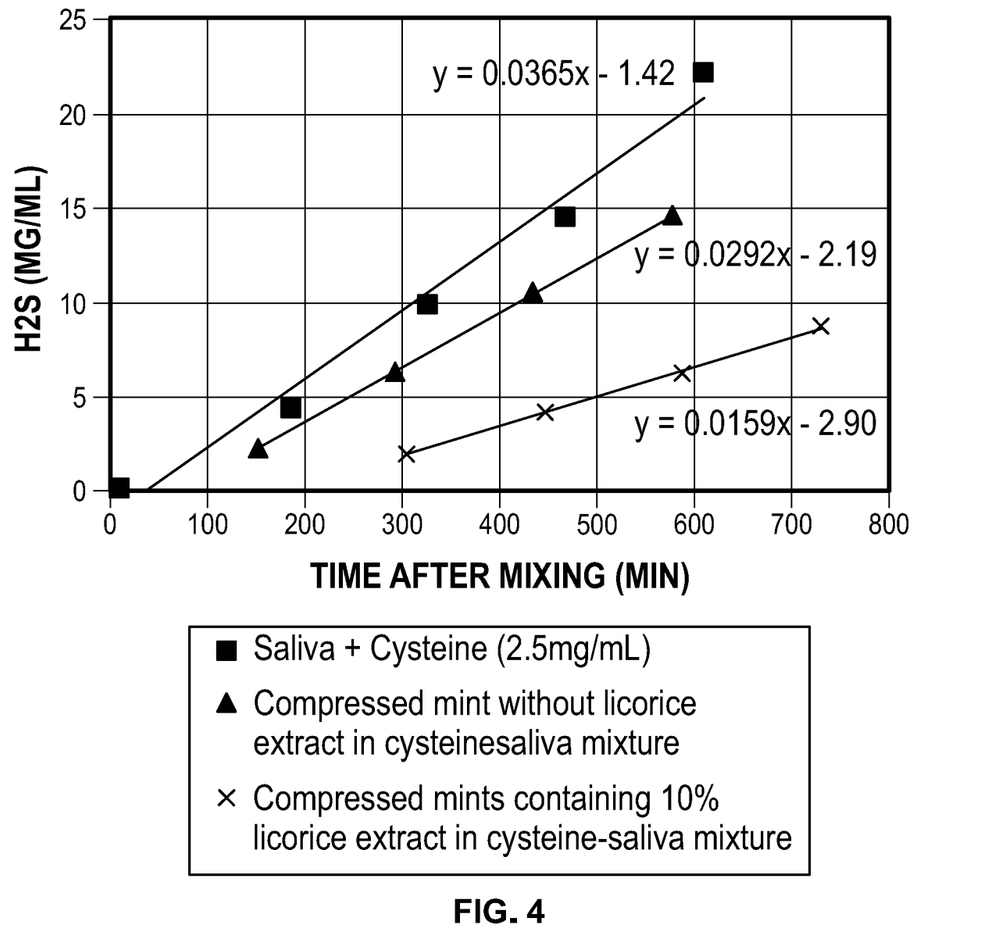
FIG. 4 provides a graphical representation of $H_2S$ produced (y-axis) over time (x-axis) in evaluating combinations of licorice extract powder and menthol in a sugar-free compressed mint application.

Licorice extract powder and menthol in combination was evaluated in a sugar-free compressed mint application. In FIG. 4, a pressed mint with a breath freshening formulation with 10 wt-% of licorice, together with 0.05 wt-% of menthol, were used. This combination outperformed a control pressed mint (formulated without any licorice powder or menthol) in the pressed mint formulation in terms of decreased $H_2S$ production over time. This example shows that a breath freshening formulation of the present disclosure are suitable for use in a compressed mint product.

Examples 5 and 6: Chewy Candy

Table 2 provides ingredients based on weight percent for two formulations of chewy candy.

TABLE 2

| Chewy Candy Ingredients | Weight % | |
|---|---|---|
| | Example 5 Formulation | Example 6 Formulation |
| Candy Mixture | | |
| Sugar | 36.5 | — |
| Corn Syrup—42 D.E. | 30.0 | — |
| Water | 10.0 | 10.0 |
| Maltitol | — | 39.0 |
| Maltitol Syrup | — | 31.39 |
| Sodium Citrate | 0.1 | 0.1 |
| Maltodextrin—18 D.E. | 0.7 | — |

TABLE 2-continued

| Chewy Candy Ingredients | Weight % | |
|---|---|---|
| | Example 5 Formulation | Example 6 Formulation |
| Maltodextrin (hydrogenated) | — | 0.7 |
| Lecithin | 0.25 | 0.25 |
| Color | 0.05 | 0.05 |
| Licorice Extract (Powder) | 10.0 | 8.0 |
| Menthol | 0.05 | 0.01 |
| Gelatin Mixture | | |
| Gelatin—150 Bloom | 1.0 | 1.0 |
| Water | 2.0 | 2.0 |
| Citric Acid (Powdered) | 2.0 | 2.0 |
| Fondant Sugar | 1.0 | — |
| Fine Maltitol Powder | — | 1.0 |
| Vegetable Fat | 6.1 | 4.0 |
| Flavor | 0.25 | 0.5 |
| Total | 100.0 | 100.0 |

First, the gelatin is dissolved in water to form the gelatin mixture. Next, the candy mixture ingredients in each Example are cooked to 225° F. (107° C.) to form a cooked candy. The gelatin mixture is added to the cooked candy, and this total mixture is whipped or pulled to incorporate air. Finally the powdered citric acid, fondant sugar, vegetable oil, and flavor are added after the whipping step. The total product is then loaded into a feeding hopper for depositing.

For a softer chewy texture, the cook temperature of the cooked candy can be reduced. The moisture content of the taffy can be altered by altering the cook temperature to meet viscosity needs of any particular depositor that is used.

Example 7: Compressed Mint

Table 3 provides ingredients based on weight percent for a formulation of a compressed mint.

TABLE 3

| Compressed Mint Ingredients | Weight % Example 7 Formulation |
|---|---|
| Sorbitol | 96.985 |
| Magnesium Stearate | 1.0 |
| Licorice Extract (Powder) | 1.0 |
| Menthol | 0.01 |
| Sweeteners | 1.0 |
| Butylated Hyroxyanisole (BHA) | 0.005 |
| Total | 100 |

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter.

Accordingly, the appended claims are intended to include within their scope such processes, machines, manufacture, compositions of matter, means, methods, or steps.

Patents, patent applications publications product descriptions, and protocols are cited throughout this application the disclosures of which are incorporated herein by reference in their entireties for all purposes.

What is claimed is:

1. A breath freshening composition comprising licorice extract and menthol, wherein the licorice extract is present in an amount of from about 3 wt-% to about 20 wt-% and a ratio of licorice extract to menthol is from about 5:1 to about 20:1.

2. The breath freshening composition of claim 1, wherein the licorice extract is present in an amount of about 10 wt-%.

3. The breath freshening composition of claim 1, wherein the menthol is present in an amount of about 0.05 wt-%.

4. The breath freshening composition of claim 1, wherein the breath freshening composition comprises about 10 wt-% licorice extract and about 0.05 wt-% menthol.

5. The breath freshening composition of claim 1, wherein the menthol is (−)-Menthol.

6. The breath freshening composition of claim 1, wherein the licorice is derived from *Glycyrrhiza glabra* and wherein the (−)-Menthol is derived from a plant of the genus *Mentha*.

7. A consumer product comprising a breath freshening composition, wherein the breath freshening composition comprises *Glycyrrhiza glabra* in an amount of about 10 wt-%, and (−)-Menthol in an amount of about 0.05 wt %,
   wherein the consumer product is selected from the group consisting of a food product, a confectionary product, and an oral product.

8. The consumer product of claim 7, wherein the confectionary product is a chewy candy.

9. The consumer product of claim 7, wherein the breath freshening composition is present in an effective amount to reduce the production of a sulfurous compound in an oral cavity.

* * * * *